United States Patent
Mochizuki et al.

(10) Patent No.: US 10,718,735 B2
(45) Date of Patent: Jul. 21, 2020

(54) GAS DETECTION METHOD, GAS DETECTION SYSTEM, AND GAS DESORPTION METHOD

(71) Applicant: FUJIFILM Corporation, Tokyo (JP)

(72) Inventors: Fumihiko Mochizuki, Kanagawa (JP); Takahiro Sano, Kanagawa (JP); Koji Takaku, Kanagawa (JP); Yasuhiro Aiki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/582,055

(22) Filed: Sep. 25, 2019

(65) Prior Publication Data

US 2020/0018720 A1    Jan. 16, 2020

Related U.S. Application Data

(63) Continuation of application No. PCT/JP2018/011090, filed on Mar. 20, 2018.

(30) Foreign Application Priority Data

Mar. 28, 2017 (JP) ................. 2017-063604

(51) Int. Cl.
*G01N 5/02* (2006.01)
*G01N 27/416* (2006.01)
(Continued)

(52) U.S. Cl.
CPC ..... *G01N 27/4162* (2013.01); *G01N 33/0009* (2013.01); *G01N 33/4836* (2013.01); *G01N 27/4075* (2013.01)

(58) Field of Classification Search
CPC .................. G01N 27/4162; G01N 33/4836
(Continued)

(56) References Cited

U.S. PATENT DOCUMENTS 8,516,880 B2 * 8/2013 Pei ................. G01N 29/036
73/24.01
2008/0298427 A1   12/2008 Gabl et al.
2010/0270153 A1   10/2010 Pei

FOREIGN PATENT DOCUMENTS

CN          102636564 A    8/2012
DE    10 2015 104 240 A1   9/2016
(Continued)

OTHER PUBLICATIONS

International Preliminary Report on Patentability dated Oct. 1, 2019 in International Application No. PCT/JP2018/011090.
(Continued)

*Primary Examiner* — Daniel S Larkin
(74) *Attorney, Agent, or Firm* — Sughrue Mion, PLLC

(57) ABSTRACT

A gas detection method using a gas detection element obtained by laminating a fixed support, a first electrode (2), a dielectric sensor (3), a second electrode (4), and a gas adsorption film (5), in this order, the method including: a step of applying a first signal resonantly driving the dielectric sensor (3) between electrodes of the first electrode (1) and the second electrode (3), and detecting gas adsorbed on the gas adsorption film based on a change of a resonant frequency of the dielectric sensor; and a step of heating the dielectric sensor (3) by applying a second signal between the electrodes after the detection of gas and desorbing gas adsorbed in the gas adsorption film; a gas detection system capable of performing the method; and a gas desorption method appropriate for applying this gas detection method.

16 Claims, 13 Drawing Sheets

(51) Int. Cl.
*G01N 33/00* (2006.01)
*G01N 33/483* (2006.01)
*G01N 27/407* (2006.01)

(58) Field of Classification Search
USPC .............................................. 73/24.01, 31.01
See application file for complete search history.

(56) References Cited

FOREIGN PATENT DOCUMENTS

| EP | 1 217 359 A1 | 6/2002 |
|----|----|----|
| JP | 56-058082 U | 5/1981 |
| JP | 7-209163 A | 8/1995 |
| JP | 2005-308404 A | 11/2005 |
| JP | 2006-258767 A | 9/2006 |
| JP | 2011-203005 A | 10/2011 |
| WO | WO 2016/174866 * | 11/2016 |

OTHER PUBLICATIONS

Written Opinion of the International Searching Authority dated Jun. 12, 2018 in International Application No. PCT/JP2018/011090, See IPRP.
International Search Report for PCT/JP2018/011090 dated Jun. 12, 2018 (PCT/ISA/210).
Extended European Search Report dated Feb. 25, 2020 for related European Patent Application No. 17886509.4.

* cited by examiner

GAS DETECTION METHOD, GAS DETECTION SYSTEM, AND GAS DESORPTION METHOD

CROSS-REFERENCE TO RELATED APPLICATIONS

This application is a Continuation of PCT International Application No. PCT/JP2018/011090 filed on Mar. 20, 2018, which claims priority under 35 U.S.C. § 119 (a) to Japanese Patent Application No. 2017-063604 filed in Japan on Mar. 28, 2017. Each of the above applications is hereby expressly incorporated by reference, in its entirety, into the present application.

BACKGROUND OF THE INVENTION

1. Field of the Invention

The present invention relates to a gas detection method, a gas detection system, and a gas desorption method.

2. Description of the Related Art

A gas detection element that detects gas floating in the air adsorbs a specific kind of gas molecules included in the air, and detects target gas by detecting the presence or absence of the adsorption and an adsorption amount. As an example of the sensor, a sensor using a mass microbalance method is known.

In the sensing by the mass micro balance method, the dielectric sensor is vibrated at a constant frequency (resonant frequency) by applying a voltage to a fine dielectric sensor (piezoelectric sensor), and a mass increase due to the gas adsorption on the surface of the dielectric sensor is detected as a decrease in resonant frequency. As a typical example of this dielectric sensor, Quartz Crystal Mass micro balance (QCM) is known.

In the QCM, electrodes are provided on both sides of a thin film of quartz cut out at a specific angle (AT-cut), and a voltage is applied, to cause shear vibration at resonant frequency in the horizontal direction with the quartz plane. Since this resonant frequency decreases according to the mass of the gas adsorbed on the electrode, it is possible to recognize the mass change of the substance on the electrode.

Besides quartz, ceramic dielectric materials (piezoelectric materials) such as lead zirconate titanate (PZT), zinc oxide (ZnO), and aluminum nitride (AlN) can be applied to the mass micro balance method. Unlike the quartz, a film can be formed with these materials by a sputtering method, a vacuum evaporation method, and the like, and there is an advantage in that a small gas detection element can be manufactured by a Micro Electro Mechanical Systems (MEMS) technique.

For example, in JP1995-209163A (JP-H07-209163A), as the gas detection element using a mass micro balance method, a gas detection sensor including a specific vibrator plate provided with a pair of electrodes, a gas adsorption film made of metal oxide formed on at least one of the electrodes, or a heater for heating the gas adsorption film is disclosed. According to the technology disclosed in JP1995-209163A (JP-H07-209163A), the adsorption gas can be desorbed by the heating of the heater, and thus, it is considered that, even in a case where the number of times of the measurement is increased, the sensitivity is not likely to decrease.

SUMMARY OF THE INVENTION

It is considered that, in the case of simultaneously detecting a plurality of gases by using a gas detection element provided with a dielectric sensor, for example, a plurality of elements of different kinds of gas adsorption films provided on the surface of the dielectric sensor are integrated, to form an array-type gas detection element. In this case, further miniaturization is required for individual elements to be integrated. The small gas detection element can be integrally manufactured by the MEMS technique, but as in JP1995-209163A (JP-H07-209163A), in an aspect in which, a heater is provided independently from the element, the target size reduction is restricted.

An object of the present invention is to provide a gas detection method capable of quickly and sufficiently desorbing (volatilizing) adsorbed gas without providing a heating member such as a heater in a gas detection method by using a mass micro balance method, and maintaining desired detection sensitivity even in a case of being repeatedly used. Another object of the present invention is to provide a gas detection system that is appropriate for performing the above gas detection method and that can miniaturize the element. Another object of the present invention is to provide a gas desorption method that is appropriate for the application to the gas detection method.

In view of the above objects, the present inventors have diligently conducted research to find that a dielectric sensor can be sufficiently heated for a short period of time by applying a specific signal different from a signal for resonantly driving the dielectric sensor, between a pair of electrodes with the dielectric sensor interposed therebetween in order to resonantly drive the dielectric sensor, and as a result, a gas adsorption film on the dielectric sensor can be effectively heated, such that the gas adsorbed on the gas adsorption film can be quickly and sufficiently desorbed. That is, it is found that, the gas adsorbed to the gas adsorption film can be efficiently removed only by controlling the signal applied between the electrodes without independently providing a heating member such as a heater, the element can be miniaturized, and rapid cooling after heating can also be realized. Further research based on these findings has been conducted to complete the present invention.

That is, the objects of the present invention have been achieved by the following means.

[1] A gas detection method using a gas detection element obtained by laminating a fixed support, a first electrode, a dielectric sensor, a second electrode, and a gas adsorption film, the method comprising:

a step of applying a first signal resonantly driving the dielectric sensor between electrodes of the first electrode and the second electrode, and detecting gas adsorbed on the gas adsorption film based on a change of a resonant frequency of the dielectric sensor; and a step of heating the dielectric sensor by applying a second signal between the electrodes, to thereby heat the second electrode on the dielectric sensor and the gas adsorption film on the second electrode after the detection of gas to desorb the gas adsorbed on the gas adsorption film.

[2] The gas detection method according to [1], in which the first signal and the second signal are alternating voltages.

[3] The gas detection method according to [2], in which a frequency of the second signal is higher than a frequency of the first signal.

[4] The gas detection method according to [2] or [3], in which a voltage of the second signal is higher than a voltage of the first signal.

[5] The gas detection method according to any one of [1] to [4], in which the dielectric sensor is formed of a ceramic dielectric material.

[6] The gas detection method according to any one of [1] to [5], in which the dielectric sensor is formed of a dielectric material selected from lead zirconate titanate, lead zirconate titanate doped with niobium, zinc oxide, and aluminum nitride.

[7] The gas detection method according to any one of [1] to [6], in which the gas adsorption film is formed of an organic material.

[8] A gas detection method using two or more gas detection elements, each of the gas detection elements being obtained by laminating a fixed support, a first electrode, a dielectric sensor, a second electrode, and a gas adsorption film, in this order, the method comprising:

a step of applying a first signal resonantly driving the dielectric sensor between electrodes of the first electrode and the second electrode of each of the gas detection elements, and detecting gas adsorbed on the gas adsorption film of each of the gas detection elements based on a change of a resonant frequency of the dielectric sensor; and a step of heating the dielectric sensor of each of the gas detection elements, after the detection of gas, by applying a second signal between the electrodes, to thereby heat the second electrode on the dielectric sensor and the gas adsorption film on the second electrode to desorb the gas adsorbed on the gas adsorption film;

wherein a constituent material forming the gas adsorption film of each of the gas detection elements is different from the other detection elements.

[9] A gas detection system comprising: a gas detection element obtained by laminating a fixed support, a first electrode, a dielectric sensor, a second electrode, and a gas adsorption film, in this order;

first signal applying means for applying a first signal resonantly driving the dielectric sensor between electrodes of the first electrode and the second electrode;

resonant frequency measuring means for measuring resonant frequency of the dielectric sensor resonantly driven by application of the first signal; and second signal applying means for applying a second signal of heating the dielectric sensor between the electrodes of the first electrode and the second electrode, to thereby heat the second electrode on the dielectric sensor and the gas adsorption film on the second electrode.

[10] The gas detection system according to [9], in which the first signal and the second signal are alternating voltages.

[11] The gas detection system according to [10], in which a frequency of the second signal is higher than a frequency of the first signal.

[12] The gas detection method according to [10] or [11], in which a voltage of the second signal is higher than a voltage of the first signal.

[13] The gas detection system according to any one of [9] to [12], in which the dielectric sensor is formed of a ceramic dielectric material.

[14] The gas detection system according to any one of [9] to [13], in which the dielectric sensor is formed of a dielectric material selected from lead zirconate titanate, lead zirconate titanate doped with niobium, zinc oxide, and aluminum nitride.

[15] The gas detection system according to any one of [9] to [14], in which the gas adsorption film is formed of an organic material.

[16] A gas detection system comprising, two or more gas detection elements, each of the gas detection elements being obtained by laminating a fixed support, a first electrode, a dielectric sensor, a second electrode, and a gas adsorption film, in this order;

first signal applying means for applying a first signal resonantly driving the dielectric sensor between electrodes of the first electrode and the second electrode of each of the gas detection elements;

resonant frequency measuring means for measuring resonant frequency of each of the dielectric sensors resonantly driven by application of the first signal; and second signal applying means for applying a second signal of heating the each of the dielectric sensors between the electrodes of the first electrode and the second electrode of each of the dielectric sensors, to thereby heat the second electrode on the dielectric sensor and the gas adsorption film on the second electrode of each of the dielectric sensors;

wherein a constituent material forming the gas adsorption film of each of the gas detection elements is different from the other detection elements.

[17] A gas desorption method of desorbing gas adsorbed on a gas adsorption film in a gas detection element obtained by laminating a fixed support, a first electrode, a dielectric sensor, a second electrode, and the gas adsorption film, in this order, the method comprising:

heating the dielectric sensor by applying a signal between electrodes of the first electrode and the second electrode and desorbing gas adsorbed on the gas adsorption film.

[18] The gas desorption method according to [17], in which the signal for heating the dielectric sensor is an alternating voltage.

[19] The gas desorption method according to [18], in which a frequency of the alternating voltage for heating the dielectric sensor is higher than the frequency of the alternating voltage for resonantly driving the dielectric sensor.

[20] The gas desorption method according to [18] or [19], in which a voltage of the alternating voltage for heating the dielectric sensor is higher than a voltage of the alternating voltage for resonantly driving the dielectric sensor.

[21] The gas desorption method according to any one of [17] to [20], in which the dielectric sensor is formed of a ceramic dielectric material.

[22] The gas desorption method according to any one of [17] to [21], in which the dielectric sensor is formed of a dielectric material selected from lead zirconate titanate, lead zirconate titanate doped with niobium, zinc oxide, and aluminum nitride.

[23] The gas desorption method according to any one of [17] to [22], in which the gas adsorption film is formed of an organic material.

In the present specification, a numerical range indicated by using "to" means a range including numerical values described before and after "to" as a lower limit value and an upper limit value.

In the gas detection method according to the embodiment of the present invention, only by controlling a signal applied between electrodes without providing a heating member such as a heater, it is possible to quickly and sufficiently desorb gas adsorbed on a gas adsorption film and thus it is possible to maintain desired detection sensitivity even in a case of being repeated used. The gas detection system according to the embodiment of the present invention can be appropriately used for implementation of the gas detection method. The gas desorption method according to the embodiment of the present invention is appropriate as a gas desorption step in the gas detection method.

BRIEF DESCRIPTION OF THE DRAWINGS

FIG. 2O is a cross-sectional view schematically illustrating a state in which a $SiO_2$ film is removed by dry-etching from a lower surface of the substrate in the flow of manufacturing the gas detection element manufactured in the example.

DESCRIPTION OF THE PREFERRED EMBODIMENTS

The preferable embodiment of the present invention is provided below, but the present invention is not limited to these embodiments.

[Gas Detection Method]

Figure 1:
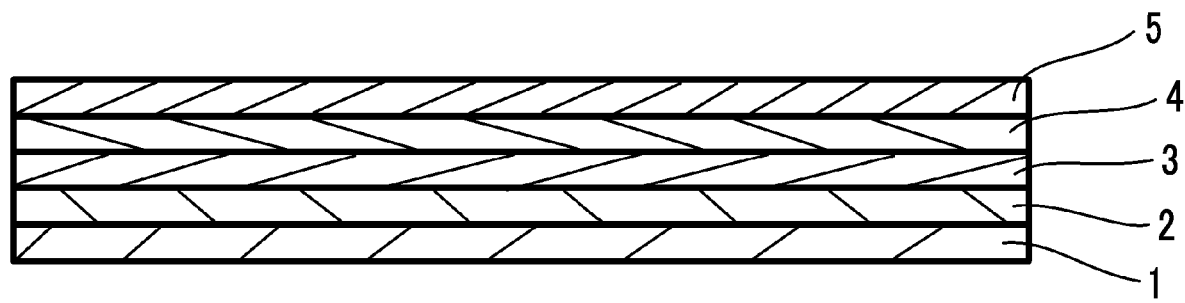
FIG. 1 is a cross-sectional view schematically illustrating a lamination structure of a gas detection element according to the present invention.

In the gas detection method according to the embodiment of the present invention, a gas detection element in which a fixed support, a first electrode, a dielectric sensor, a second electrode, and a gas adsorption film are laminated in this order. For example, the gas detection element is preferably formed by the MEMS technique. A cross-sectional view schematically illustrating a lamination structure of a gas detection element used in the present invention is illustrated in FIG. 1. FIG. 1 illustrates a lamination structure in which a first electrode 2, a dielectric sensor 3, a second electrode 4, and a gas adsorption film 5 are sequentially provided on a support 1.

Each member constituting the gas detection element used in the present invention is described.

<Support>

The support (hereinafter, also referred to as a substrate) is a member that is responsible for supporting the gas sensor element used in the present invention. The support is not particularly limited, as long as the support can be fixed and support elements. Examples thereof include a silicon substrate, a glass substrate, a resin substrate, and a ceramic substrate, and in consideration of manufacturing of an element by the MEMS technique, a silicon substrate is preferable, and among these, a silicon on insulator (SOI) substrate can be appropriately used. It is preferable to use an SOI substrate since it is possible to reduce the process in a case of manufacturing of the element.

The thickness of the support preferably 0.2 to 1,000 mm, more preferably 0.2 to 100 mm, even more preferably 0.2 to 10 mm, and particularly preferably 0.2 to 0.4 mm.

<First Electrode>

The first electrode is an electrode for applying an electric field to a dielectric sensor described below. The first electrode requires adhesiveness to a constituent material of the substrate and a constituent material of the dielectric sensor. As the material, titanium (Ti), iridium (Ir), platinum (Pt), gold (Au), molybdenum (Mo), tungsten (W), tantalum (Ta), or the like can be appropriately used. The first electrode can be formed by depositing these materials on a support by sputtering, vacuum evaporation, or the like. The first electrode can also be formed by inkjet printing by using metal ink.

The thickness of the first electrode is preferably 50 to 500 nm and more preferably 100 to 200 nm.

<Dielectric Sensor>

The constituent material of the dielectric sensor is not particularly limited, as long as the constituent material can be resonantly driven by applying a specific signal. For example, a crystal resonator can be used, and a ceramic dielectric material can also be used. In consideration of using the gas detection element of the present invention as a MEMS device, the dielectric sensor is preferably a ceramic dielectric material, and for example, one or more kinds of perovskite-type oxide represented by Formula (1) are preferably used.

$$XZO_3 \qquad (1)$$

X represents at least one kind of atoms including Pb.

Z represents at least one atom selected from the group consisting of Ti, Zr, V, Nb, Ta, Sb, Cr, Mo, W, Mn, Sc, Co, Cu, In, Sn, Ga, Zn, Cd, Fe, and Ni.

O is an oxygen atom.

In the perovskite-type oxide of Formula (1), the form in which X:Y:O (molar ratio) is 1:1:3 is the standard, but the molar ratio of the perovskite-type oxide of Formula (1) may be deviated from the molar ratio of the above standard molar ratio in the range of obtaining the perovskite structure. That is, in a perovskite compound of Formula (1), other atoms may be doped at a ratio of 30% or less with respect to the total number of moles of X, Y, and O.

Specific examples of the perovskite type oxide represented by Formula (1) include lead containing compounds such as lead titanate, lead zirconate titanate (PZT), lead zirconate, lead titanate lanthanum, zirconate lead titanate lanthanum, magnesium niobate zirconate lead titanate, nickel niobate zirconate lead titanate, and zinc niobate zirconate lead titanate, and mixed crystal systems thereof.

The constituent material of the dielectric sensor of the present invention is preferably represented by Formula (2).

$$X_a(Zr_x,Ti_y,M_{b-x-y})_bO_c \qquad (2)$$

X represents at least one atom including Pb.

M represents at least one atoms selected from the group consisting of V, Nb, Ta, Sb, Mo, and W.

x,y, and b satisfy the following formula.

$$0<x<b,\ 0<y<b,\ 0\le b-x-y$$

a:b:c=1:1:3 (molar ratio) is the standard, but the value may be deviated from the above standard ratio in the range of obtaining the perovskite structure. That is, in the perovskite compound of Formula (2), other atoms may be doped at a ratio of 30% or less with respect to the total number of moles of X, Zr, Ti, M, and O described above.

The perovskite-type oxide of Formula (2) is oxide in which intrinsic PZT or a portion of a B site of PZT is substituted by M. M is an atom having a higher valence than tetra-valent Zr and Ti in the perovskite-type crystal structure, and it is known that PZT doped with M can enhance properties such as piezoelectric performances than intrinsic PZT.

The upper limit of b-x-y is not particularly limited as long as the upper limit is in the range in which the perovskite structure can be obtained. For example, in a case where M is Nb, the Nb/(Zr+Ti+Nb) molar ratio is preferably 0.05 to 0.25 and more preferably 0.06 to 0.20.

A film formed of a perovskite-type oxide represented by each of Formulae (1) and (2) has a high piezoelectric strain constant (d31 constant), and thus the piezoelectric actuator provided with this film has excellent variation characteristics. Among these, lead zirconate titanate (PZTN) doped with Nb by about 12% by atomic composition percentage may be vapor-deposited to form a film, such that the film satisfies, for example, a piezoelectric strain constant d31=250 pm/V.

An actuator provided with the film formed of perovskite-type oxide represented by each of Formulae (1) and (2) has more clear relationship with a voltage and a displacement characteristic and has excellent in sensor characteristics.

In addition to the above, as the constituent material of the dielectric sensor used in the present invention, non-lead containing compounds such as barium titanate, strontium barium titanate, bismuth sodium titanate, bismuth potassium titanate, sodium niobate, potassium niobate, lithium niobate, and bismuth ferrite, and mixed crystal systems thereof may be used. $BaTiO_3$, $KaNaNbO_3$, $BiFeO_3$, and the like can be used, and non-perovskite-type materials such as aluminum nitride (AlN), zinc oxide (ZnO) or the like can be used.

It is preferable that the dielectric sensor of the present invention is formed of a dielectric material selected from lead zirconate titanate, lead zirconate titanate doped with niobium, zinc oxide, and aluminum nitride.

It is preferable that a film can be formed with the constituent material of the dielectric sensor on the first electrode by a sputtering method, a vapor deposition method, or the like to form a dielectric sensor.

The thickness of the dielectric sensor is preferably 0.1 to 10 μm and more preferably 1 to 3 μm.

<Second Electrode>

The second electrode is provided on the dielectric sensor as an electrode for applying an electric field to the dielectric sensor, together with the first electrode. As the constituent material of the second electrode, a material having high adhesiveness to the dielectric sensor is preferable, and titanium (Ti), iridium (Ir), platinum (Pt), gold (Au), molybdenum (Mo), tungsten (W), tantalum (Ta), or the like can be used. The second electrode can be formed by vapor-depositing these material on the dielectric sensor by a sputtering method, a vapor deposition method, or the like. The second electrode can also be formed by inkjet printing using metal ink.

The thickness of the second electrode is preferably 50 to 500 nm and more preferably 100 to 200 nm.

<Gas Adsorption Film>

The constituent material of the gas adsorption film is not particularly limited, as long as the constituent material has adsorption ability to the gas to be detected, and is appropriately selected according to the kind of gas to be detected. The constituent material of the gas adsorption film may be an inorganic material or an organic material, and is preferably an organic material in view of gas adsorption selectivity. The organic material is not particularly limited, and examples thereof include polyethylene (PE), polyisobutylene (PIB), polyethylene vinyl acetate (PEV), and polyvinyl alcohol (PVA), but the present invention is limited to these aspects. As the gas adsorption film, a coloring agent material can also be used.

Examples of the inorganic materials that can be used as the gas adsorption film include $SiO_2$, SiN, SiON, $Al_2O_3$, $HfO_2$, $Ta_2O_5$, and $Ga_2O_3$.

Generally, as the constituent material of the gas adsorption film, there is tendency in that the gas adsorptivity of the gas adsorption film is further enhanced by selecting a material having an SP value close to the solubility parameter (SP value) of the gas to be detected.

The gas adsorption film can be formed by various coating methods. For example, a coating solution obtained by dissolving the constituent material of the gas adsorption film is prepared, the first electrode is coated with the coating solution to form a coating film, and the coating film is dried, to form a gas adsorption film. The coating method is not particularly limited, and an inkjet method, the dip coating method, a spin coating method, or the like can be employed. In view of enabling film formation with higher accuracy, an ink jet method is more preferable.

The thickness of the gas adsorption film is preferably 0.01 to 5 μm and more preferably 0.05 to 1 μm.

The gas detection element used in the present invention is preferably manufactured by the MEMS technique. By using the MEMS technique, the element can be miniaturized and thus the integration of the element becomes possible. As a result, high sensitivity of gas detection, improvement in reliability, multi-detection of a plurality of kinds of gas, and the like become possible.

Subsequently, a gas detection step and an adsorbed gas desorption step that constitute the gas detection method according to the embodiment of the present invention are described.

<Gas Detection Step>

The gas detection method according to the embodiment of the present invention includes a step (gas detection step) of applying a first signal that resonantly drives the dielectric sensor between electrodes of the first electrode and the second electrode and detecting gas adsorbed on the gas adsorption film based on the change of the resonant frequency (resonance vibration frequency) of the dielectric sensor.

The first signal is usually an alternating voltage, and the dielectric sensor is resonantly driven by applying the first signal. In this state, in a case where the element is exposed to the gas to be detected and the gas to be detected is adsorbed on the gas adsorption film, a mass of the gas adsorption film is increased. As a result, the load applied to the dielectric sensor is increased by the amount of gas adsorption, and the resonant frequency of the resonantly driven dielectric sensor is lowered. Therefore, the gas can be detected by detecting the change in the resonant frequency of the resonantly driven dielectric sensor.

The first signal is transmitted from a transmission source of the first signal. As the transmission source of the first signal, a general function generator, an oscillator (IC), an oscillation circuit, or the like can be used.

For example, the resonant frequency of the dielectric sensor can be measured by using an impedance analyzer, a spectro analyzer, a frequency counter, an oscilloscope, a laser doppler displacement meter, or the like. The impedance analyzer is preferable because the impedance analyzer can also be used as a transmission source of a resonant drive signal (first signal) of the dielectric sensor.

In the gas detection method according to the embodiment of the present invention, it is also preferable to use two or more elements having different constituent materials of the gas adsorption film as the gas detection element. In a case where two or more elements having different constituent materials of the gas adsorption film are used, a plurality of kinds of gases can be detected at one time. It is also possible to identify the kind of gas by creating a database of the relationship between the vibration frequency pattern of the dielectric sensor and the kind of gas in each of the plurality of elements.

<Adsorbed Gas Desorption Step>

The gas detection method according to the embodiment of the present invention includes a step (adsorbed gas volatilizing step) of heating the dielectric sensor by applying a second signal between the electrodes after the gas detection step is completed and desorbing the gas adsorbed on the gas adsorption film.

The second signal is usually an alternating voltage, and the dielectric sensor can be efficiently heated in a short period of time, by applying the second signal. The second signal is different from the first signal in that the second signal is not a signal for resonantly driving the dielectric sensor. That is, the second signal is usually an alternating voltage having a frequency higher than the first signal or a signal having a voltage higher than the alternating voltage of the first signal. It is preferable that the second signal has a higher frequency and a higher voltage than the first signal. The dielectric sensor cannot convert the second signal into resonant drive energy, and the second signal applied to the dielectric sensor is converted into thermal energy by dielectric loss.

In a case where the dielectric sensor is heated by the application of the second signal, the gas adsorption film is heated via the first electrode provided thereon so as to cause the gas adsorbed on the gas adsorption film to be sufficiently desorbed (for example, the adsorbed gas can be desorbed in several seconds to one minute) and to regenerate the gas adsorption film to the initial state (state without gas adsorption). That is, unlike an aspect in which a heating member such as a heater is separately provided, degassing can be performed easily and quickly with less electric power.

The heat capacity of the element of the laminated structure defined in the present invention is small, the element is quickly heated by the application of the second signal, and is naturally and quickly cooled in a case where the application of the second signal is stopped (for example, the temperature can be returned to the temperature before heating for several seconds).

In the desorption step of the adsorbed gas, the heating temperature of the dielectric sensor according to the second signal can be adjusted by the frequency or the voltage level of the second signal, and is appropriately adjusted according to the kind of gas to be desorbed.

The second signal is transmitted from the transmission source of the second signal. As the transmission source of the second signal, a general function generator, an oscillator (IC), an oscillation circuit, or the like can be used.

Since the gas adsorption film is so-called initialized (for example, the resonant frequency can be returned to that within ±2 Hz of the resonant frequency in the initial state) by the desorption step of the adsorbed gas, the gas detection element becomes a state of capable of performing next gas detection. The level of desorption (removal) of gas from the gas adsorption film can be checked by measuring the resonant frequency of the dielectric sensor by application of the first signal.

According to the gas detection method according to the embodiment of the present invention, the desorption process of the adsorption gas can be quickly performed, and thus the measurement efficiency can be further improved.

[Gas Detection System]

The gas detection system according to the embodiment of the present invention is a system appropriate for performing the gas detection method according to the embodiment of the present invention, and includes a gas detection element obtained by laminating a first electrode, a dielectric sensor, a second electrode, and a gas adsorption film, in this order;

first signal applying means for applying a first signal that resonantly drives the dielectric sensor between electrodes of the first electrode and the second electrode;

resonant frequency measuring means for measuring a resonant frequency of the dielectric sensor resonantly driven by application of the first signal; and second signal applying means for applying the second signal for heating the dielectric sensor between the electrodes of the first electrode and the second electrode.

The aspects of the first electrode, the dielectric sensor, the second electrode, and the gas adsorption film are the same as the aspects described in the gas detection method according to the embodiment of the present invention described above. The first signal and the second signal are also respectively the same as the first signal and the second signal described in the gas detection method according to the embodiment of the present invention. As the resonant frequency measuring means, the impedance analyzer or the like described above can be used.

In the gas detection system according to the present invention, the first signal applying means and the second signal applying means can be carried by one device (for example, one device having both the first signal applying means and the second signal applying means can also be employed). As described above, a device used as the signal applying means can be used also as the resonant frequency measuring means. Separate devices may be respectively adopted as the first signal applying means, the resonant frequency measuring means, and the second signal applying means.

The device that can be used as the signal applying means is as described above.

The gas detection system according to the embodiment of the present invention may have other configurations as long as the gas detection system has the configurations defined by the present invention. For example, a container (a chamber such as a metal housing or a resin housing) for storing the gas detection element may be included.

[Gas Desorption Method]

The gas desorption method according to the embodiment of the present invention is a method of desorbing gas adsorbed on the gas adsorption film of the gas detection element including the first electrode, the dielectric sensor, the second electrode, and the gas adsorption film laminated in this order, and includes heating the dielectric sensor by applying a signal between the electrodes of the first electrode and the second electrode and desorbing gas adsorbed on the gas adsorption film.

In the gas desorption method according to the embodiment of the present invention, aspects of the first electrode, the dielectric sensor, the second electrode, and the gas adsorption film are as described in the gas detection method according to the embodiment of the present invention. The signal applied between the electrodes is the same as the aspect of the second signal described in the gas detection method according to the embodiment of the present invention.

The gas desorption method according to the embodiment of the present invention can be applied to the desorption step of the adsorbed gas in the gas detection method according to the embodiment of the present invention.

EXAMPLES

The present invention is specifically described based on the examples, but the present invention is not limited to these aspects.

[Manufacturing Gas Detection Element]

Figure 2A:
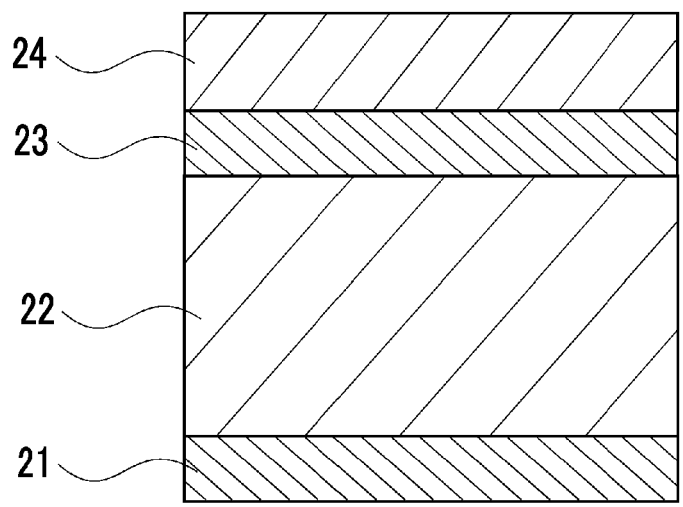
FIG. 2A is a cross-sectional view schematically illustrating an SOI substrate of a gas detection element manufactured in an example.
Figure 2B:
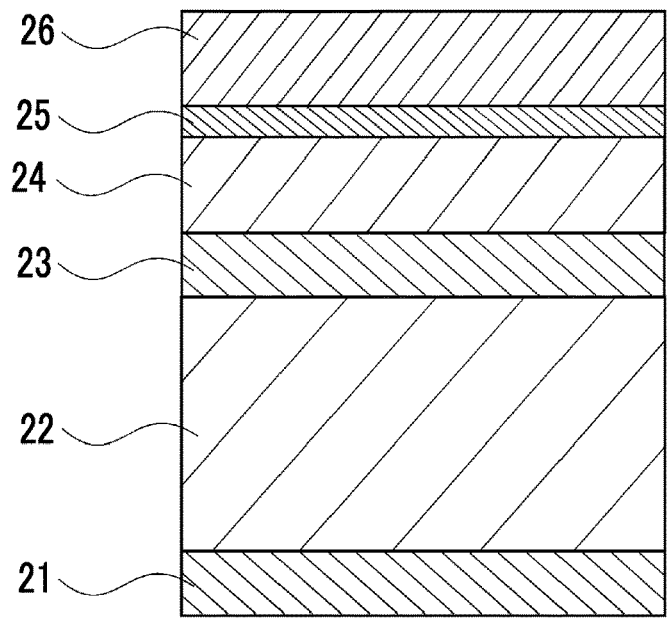
FIG. 2B is a cross-sectional view schematically illustrating a state in which, in a flow of manufacturing the gas detection element manufactured in the example, a first electrode is provided on the SOI substrate, and a PZTN film is provided on the first electrode.
Figure 2C:
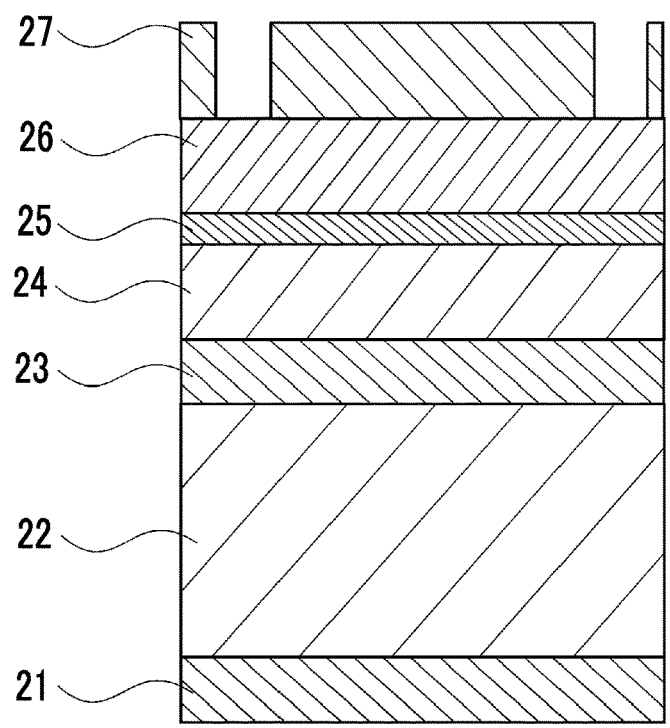
FIG. 2C is cross-sectional view schematically illustrating a state in which resist patterning is performed on the PZTN film in the flow of manufacturing the gas detection element manufactured in the example.
Figure 2D:
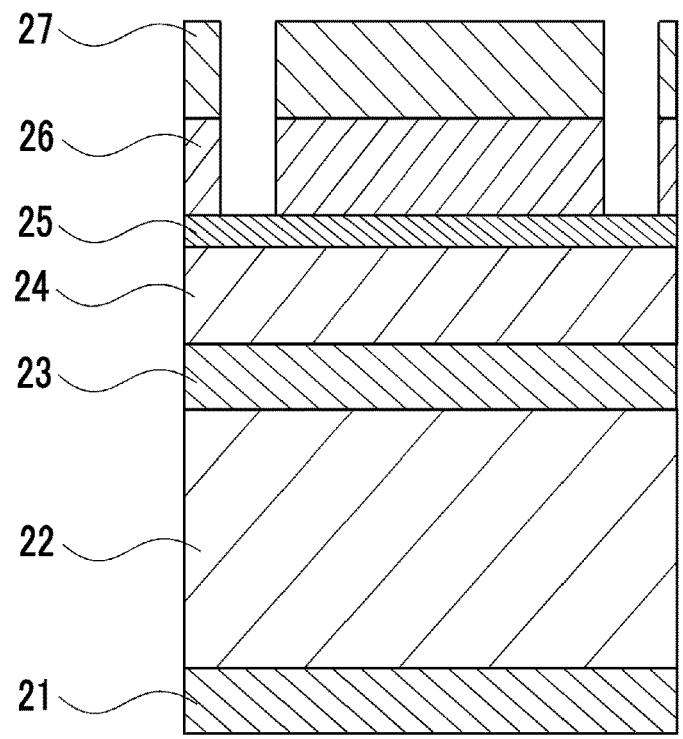
FIG. 2D is a cross-sectional view schematically illustrating a state in which the PZTN film is wet-etched in the flow of manufacturing the gas detection element manufactured in the example.
Figure 2E:
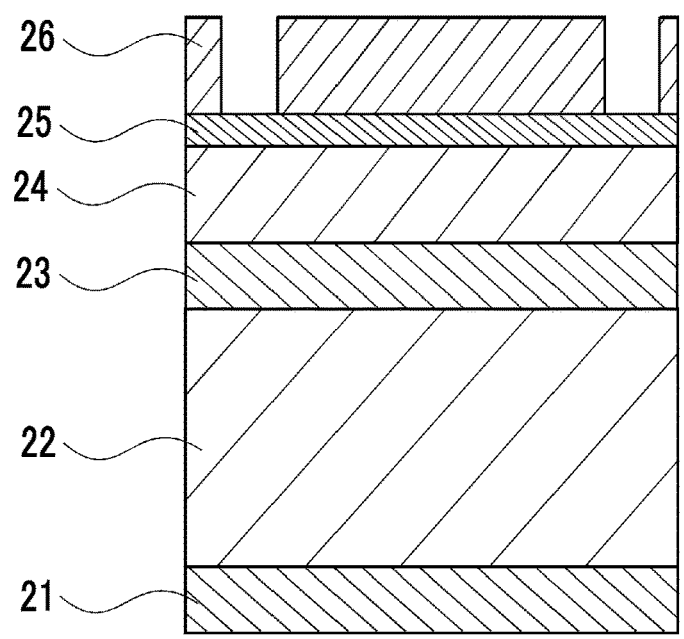
FIG. 2E is a cross-sectional view schematically illustrating a state in which the PZTN film is wet-etched and then the resist is removed using a resist removing solution in the flow of manufacturing the gas detection element manufactured in the example.
Figure 2F:
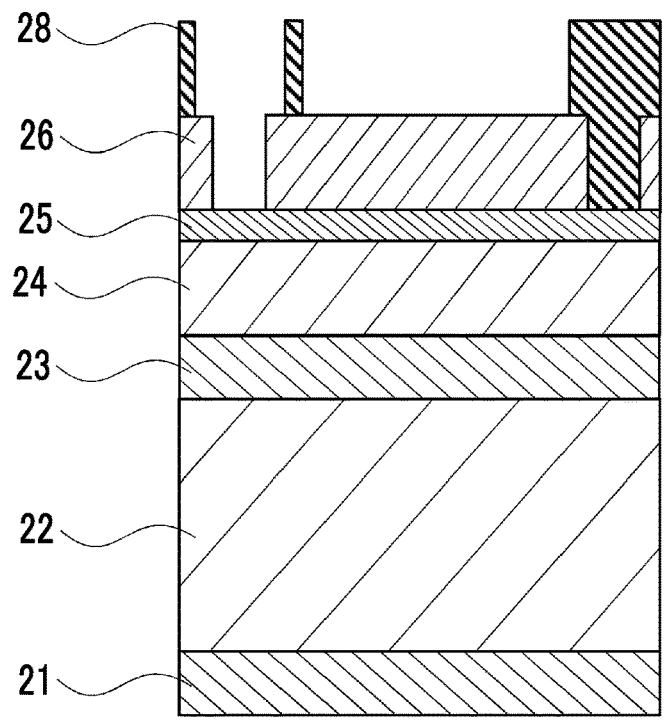
FIG. 2F is a cross-sectional view schematically illustrating a state in which resist patterning for forming a contact with the first electrode and for forming the second electrode in the flow of manufacturing the gas detection element manufactured in the example.
Figure 2G:
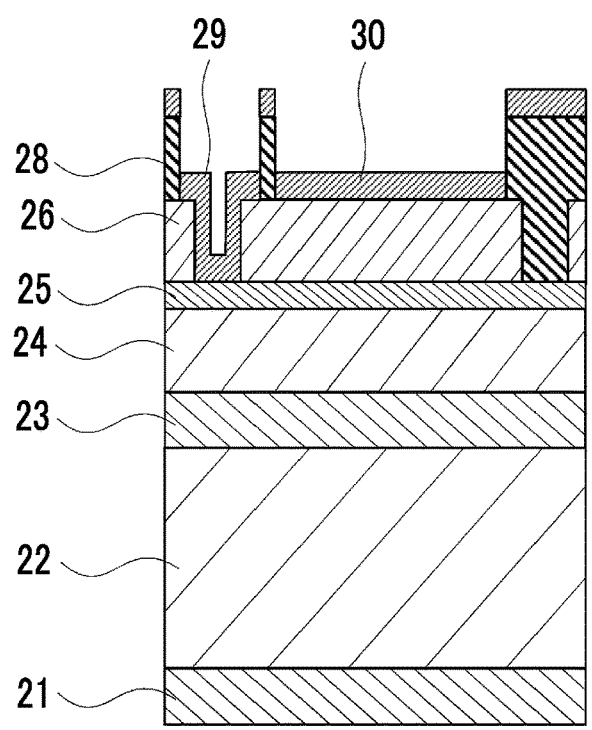
FIG. 2G is a cross-sectional view schematically illustrating a state in which the contact with the first electrode and the second electrode in the flow of manufacturing the gas detection element manufactured in the example.
Figure 2H:
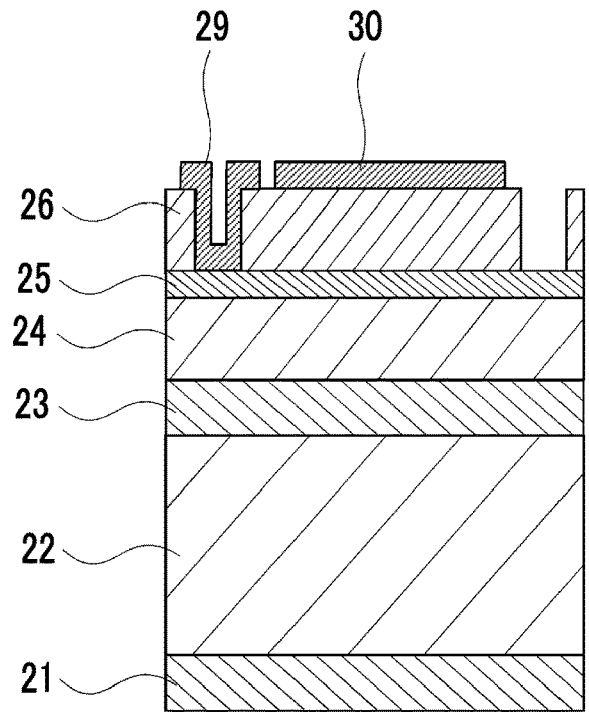
FIG. 2H is a cross-sectional view schematically illustrating a state in which a resist is removed by using a resist removing solution after the contact with the first electrode and the second electrode in the flow of manufacturing the gas detection element manufactured in the example.
Figure 2I:
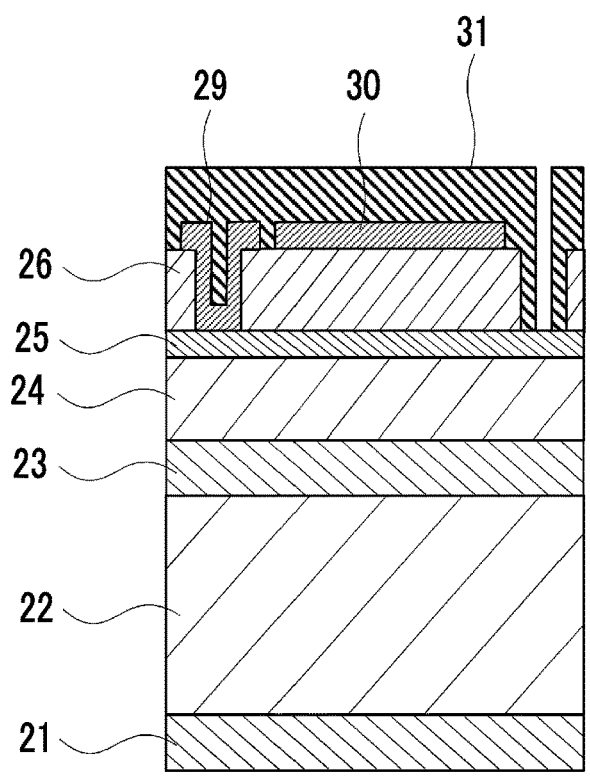
FIG. 2I is a cross-sectional view schematically illustrating a state in which resist patterning for patterning the first electrode and a surface layer (15 μm Si film) of the substrate is performed in the flow of manufacturing the gas detection element manufactured in the example.
Figure 2J:
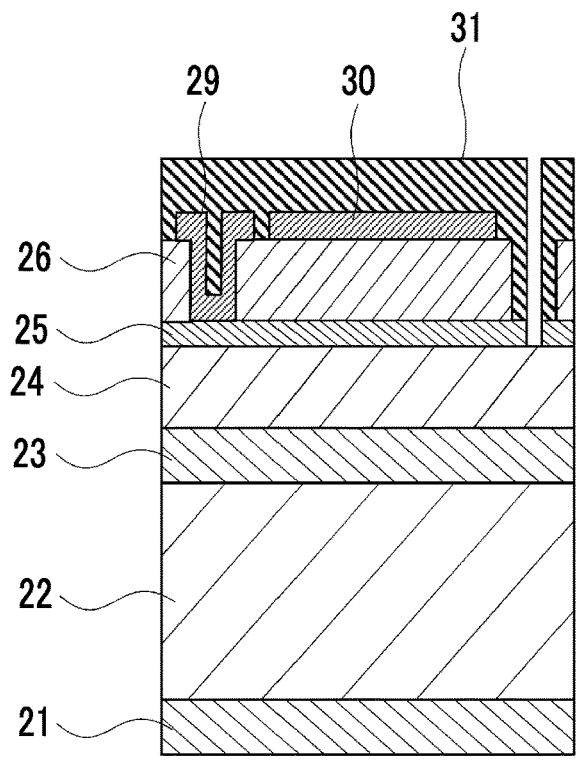
FIG. 2J is a cross-sectional view schematically illustrating a state in which a portion of the first electrode is removed by dry etching in the flow of manufacturing the gas detection element manufactured in the example.
Figure 2K:
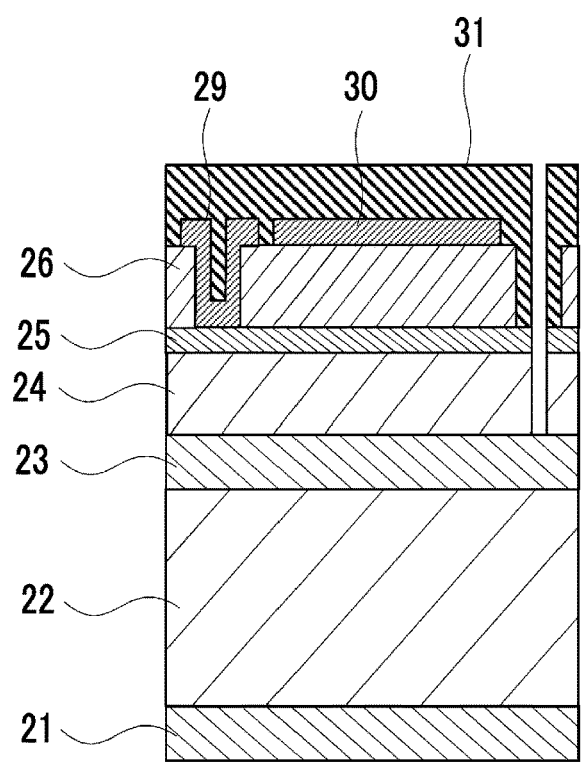
FIG. 2K is a cross-sectional view schematically illustrating a state in which a portion of the Si film is removed by etching in the flow of manufacturing the gas detection element manufactured in the example.
Figure 2L:
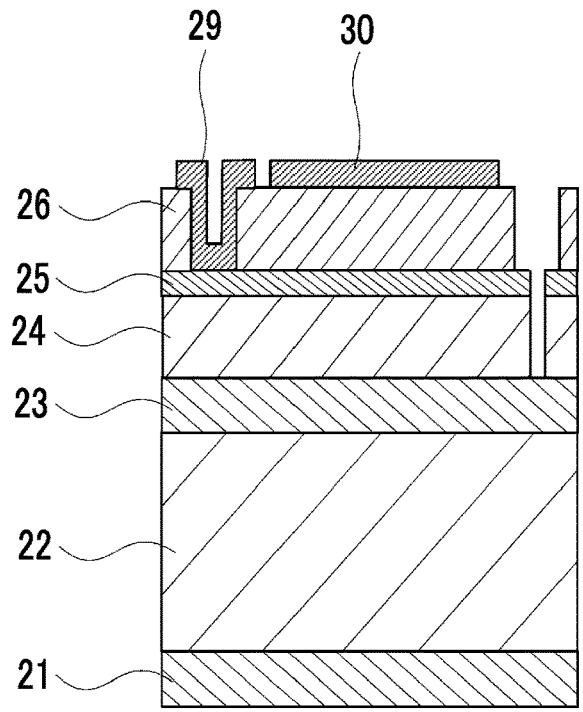
FIG. 2L is a cross-sectional view schematically illustrating a state in which after a portion of the Si film is removed by etching, a resist is removed by a resist removing solution in the flow of manufacturing the gas detection element manufactured in the example.
Figure 2M:
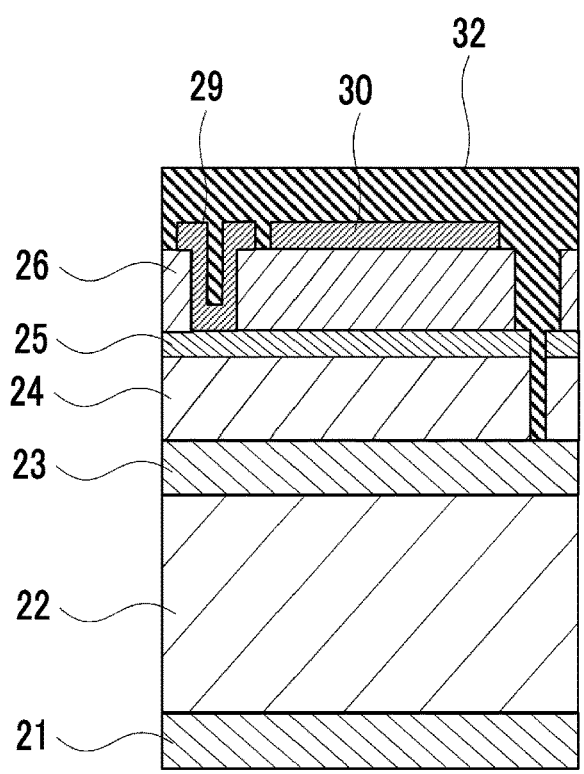
FIG. 2M is a cross-sectional view schematically illustrating a state in which a photoresist is formed on the second electrode side for the purpose of protection in subsequent steps in the flow of manufacturing the gas detection element manufactured in the example.
Figure 2N:
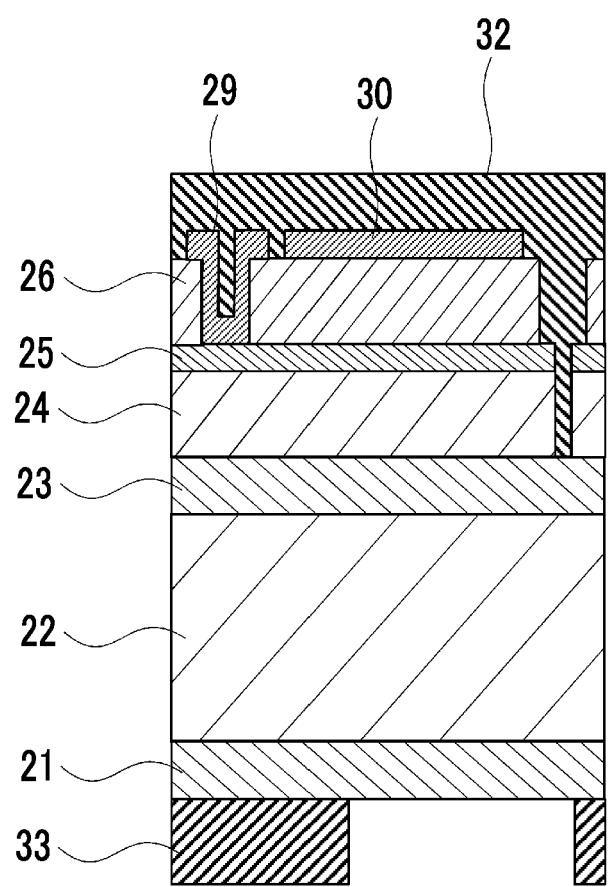
FIG. 2N is a cross-sectional view schematically illustrating a state in which a resist patterning is performed for patterning a lower surface of the substrate in the flow of manufacturing the gas detection element manufactured in the example.
Figure 20:
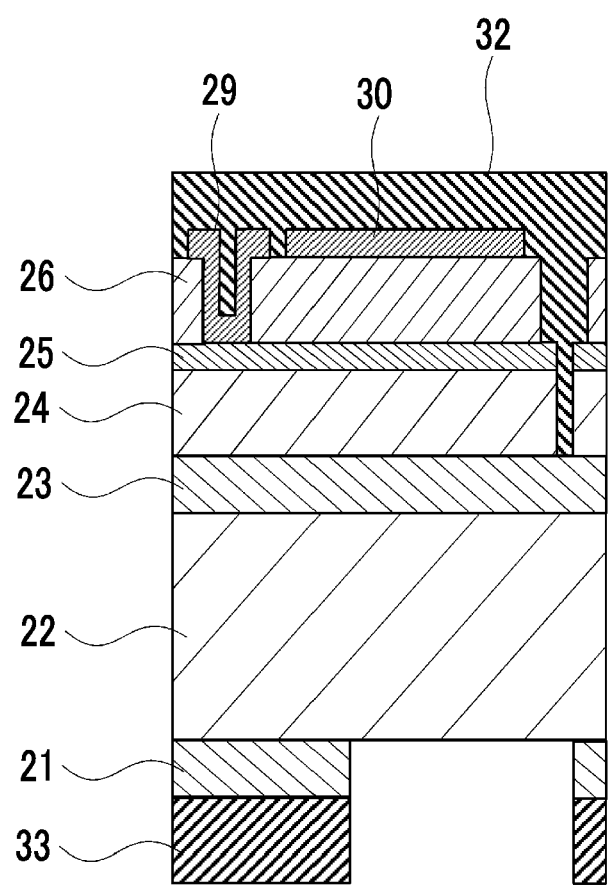
Figure 2P:
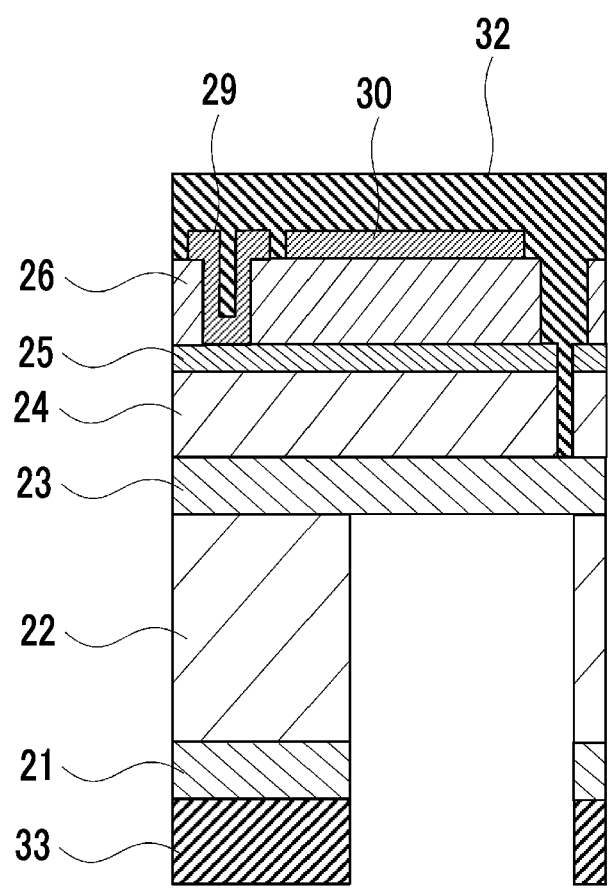
FIG. 2P is a cross-sectional view schematically illustrating a state in which the Si film is removed by dry-etching from the lower surface of the substrate in the flow of manufacturing the gas detection element manufactured in the example.
Figure 2Q:
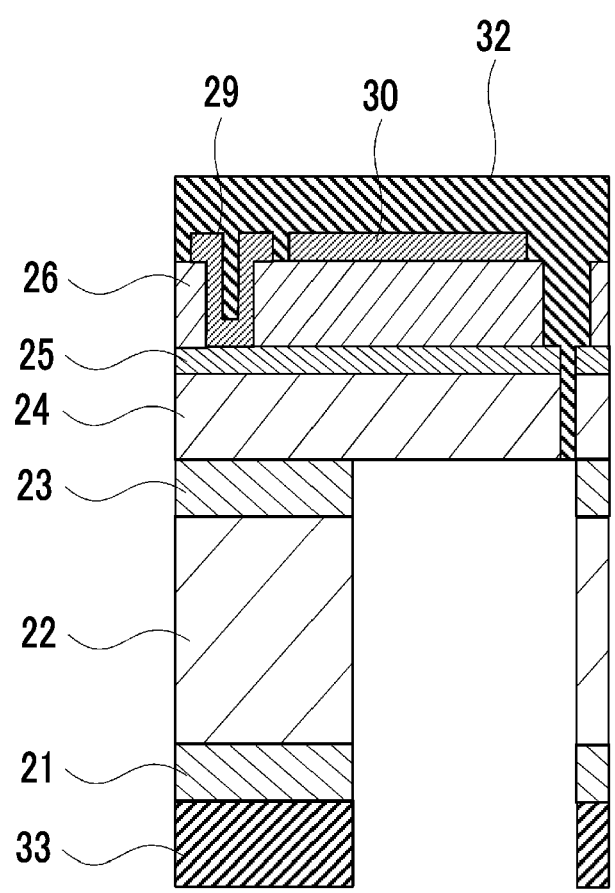
FIG. 2Q is a cross-sectional view schematically illustrating a state in which the $SiO_2$ film is removed by dry etching from the lower surface of the substrate in the flow of manufacturing the gas detection element manufactured in the example.
Figure 2R:
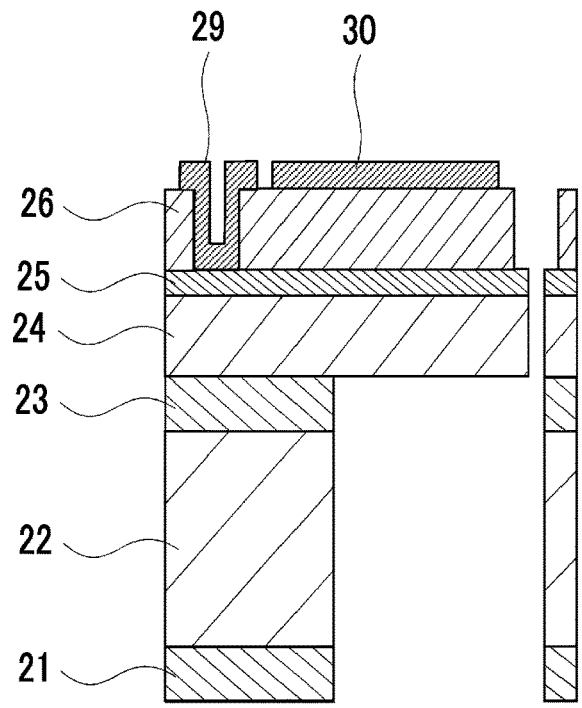
FIG. 2R is a cross-sectional view schematically illustrating a state in which, after the $SiO_2$ film is removed by dry etching from the lower surface of the substrate, and all of the resist is removed by the resist removing solution in the flow of manufacturing the gas detection element manufactured in the example.
Figure 2S:
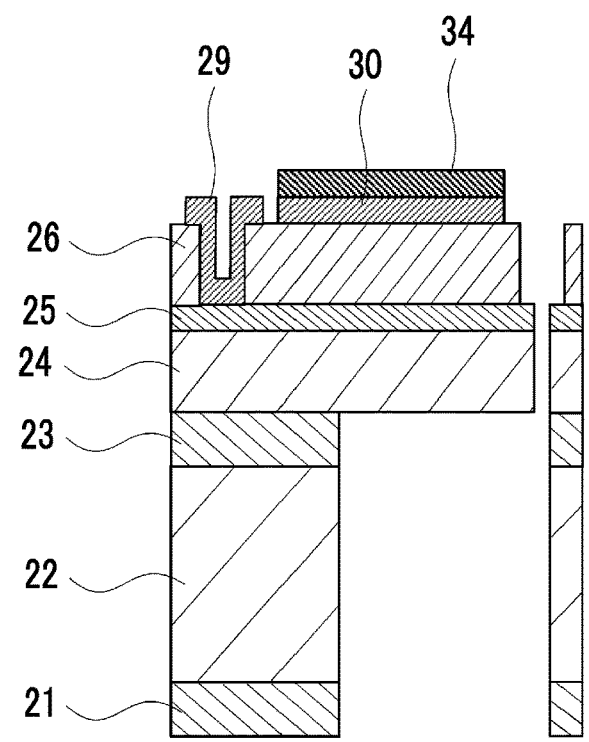
FIG. 2S is a cross-sectional view schematically illustrating a state in which a gas adsorption film is formed on the second electrode in the flow of manufacturing the gas detection element manufactured in the example.

According to the manufacturing flow schematically illustrated in FIGS. 2A to 2S, the gas detection element was manufactured. Details thereof are described.

As the substrate to be a support, the SOI substrate illustrated in FIG. 2A was used. In FIG. 2A, the substrate has a lamination structure having a $SiO_2$ film (21, thickness of 1 µm), a Si film (22, thickness of 400 µm), a $SiO_2$ film (23, thickness of 1 µm), and a Si film (24, thickness of 15 µm) in an order from the bottom.

A Ti film (thickness of 20 nm) and an Ir film (thickness of 100 nm) were continuously formed on the substrate by a DC sputtering method as a first electrode (25, lower electrode), and then a PZTN film (26, thickness of 3 µm) was formed as a dielectric sensor on the Ir film a RF sputtering method (FIG. 2B). The film forming conditions are provided below.

—First Electrode Film Forming Conditions—
Substrate heating temperature: about 350° C.
Input power: DC500W
Gas: Ar gas
Film formation pressure: 0.4 Pa
—PZTN film formation conditions—
Substrate heating temperature: about 500° C.
Input power: RF 1 kW
Gas: Ar gas:oxygen (volume ratio of 10:1)
Film formation pressure: 0.35 Pa A resist (27) was formed for patterning of the PZTN film [photoresist coat (AZ-1500, manufactured by Merck)→drying→exposure development→baking, FIG. 2C]. Subsequently, the PZTN film was wet-etched (FIG. 2D), and the resist (27) was removed by using a resist removing solution (MS2001, manufactured by Fujifilm Corporation) (FIG. 2E).

A resist (28) for forming a contact with the lower electrode and for forming the upper electrode was formed [photoresist coating (AZ-5214, manufactured by Merck) →drying→exposure→baking→negative/positive reversal exposure→development→drying, FIG. 2F].

As a contact (29) with the lower electrode and a second electrode (30, upper electrode), a Ti film (thickness of 20 nm) and an Au film (thickness of 100 nm) were continuously formed by a DC sputtering method. The film forming conditions are provided below (FIG. 2G).

—Contact with Lower Electrode and Second Electrode Film Formation Conditions—
Substrate heating temperature: room temperature
Input power: DC500W
Gas: Ar gas
Film formation pressure: 0.4 Pa Subsequently, the resist (28) was removed with a resist removing solution (MS2001, manufactured by Fujifilm Corporation), the contact (29) with the lower electrode was formed, and the upper electrode (30) was formed (FIG. 2H).

A resist (31) for lower electrode patterning and for patterning the substrate surface layer (15 µm Si film) was formed [photoresist coating (AZ-1500, manufactured by Merck)→drying→exposure→development→baking, FIG. 2I].

The lower electrode was removed by dry etching, the Si film was etched, and then the resist (31) was removed by a resist removing solution (MS 2001, manufactured by Fujifilm Corporation) (FIGS. 2J, 2K, and 2L).

A resist (32) was formed on the upper electrode side for the purpose of protection in subsequent steps (photoresist coat (AZ-10XT, manufactured by Merck)→drying→baking, FIG. 2M).

A resist (33) for patterning the lower surface of the substrate was formed [photoresist coat (AZ-3100, manufactured by Merck)→drying→exposure→development→baking, FIG. 2N].

The 1 µm $SiO_2$ film (21), the 400 µm Si film (22), and the 1 µm $SiO_2$ film (23) were removed from the lower surface of the substrate by dry etching, all the resist was removed by the resist removing solution (MS2001, manufactured by Fujifilm Corporation) (FIGS. 2O, 2P, 2Q, and 2R), and a structural body obtained in this manner and illustrated on the left side of FIG. 2R is called an element precursor.

Subsequently, a gas adsorption film 34 illustrated in FIG. 2S was formed on the upper electrode of the element precursor as follows.

<Preparation of Coating Solution for Forming Gas Adsorption Film>

Polyethylene vinyl acetate (PEVA) was dissolved in toluene to prepare a coating solution containing 1% by mass of PEVA.

<Forming Gas Adsorption Film>

The above coating solution was introduced into a cartridge (Model: DMCLCP-11610) of an ink jet printer (Model: DMP-2831, manufactured by Fujifilm Corporation).

The element precursor was subjected to a UV cleaner treatment for five minutes by using a device manufactured by Jelight Company Inc. (Model: 144AX-100). Immediately after this treatment, the coating solution was dropped by using the above ink jet printer (six droplets at a pitch of 50 µm, 10 pL jetting at one droplet, jetting speed: about 7 m/s), so as to form a coating film.

In order to completely volatilize the toluene, drying was performed at 120° C. for two hours by using a vacuum oven (VAC-100, manufactured by ESPEC CORP.).

In this manner, the gas detection element having the first electrode, the dielectric sensor, the second electrode, and the gas adsorption film formed in this order on the support and illustrated on the left side of FIG. 2S was obtained.

Test Example

Figure 3:
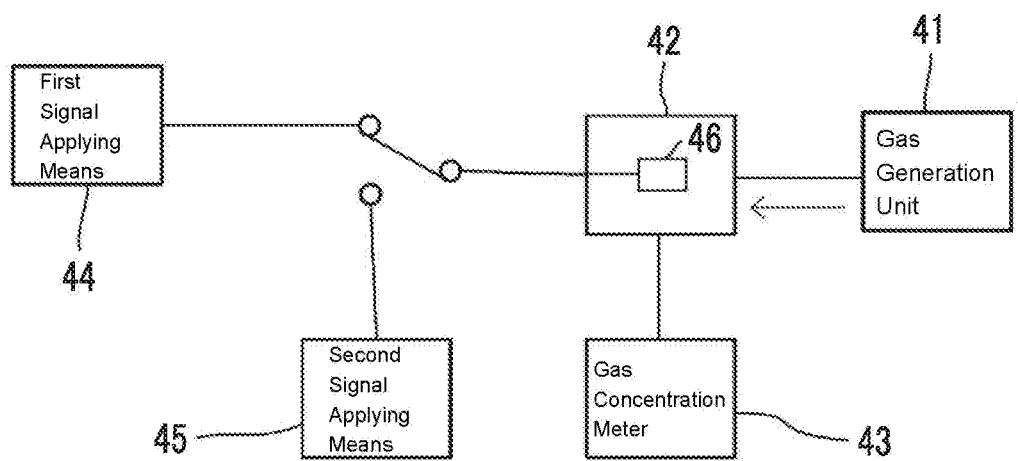
FIG. 3 is a system diagram for describing a gas detection system employed in the example.

A gas desorption test was performed by the system illustrated in FIG. 3 by using the gas detection element manufactured above. FIG. 3 is a system diagram describing a system according to the embodiment of the present invention.

<Gas Generation Unit 41>

As the gas generation unit 41, TM-1028 manufactured by HORIBA STEC, Co., Ltd was used, to supply the target gas to a chamber 42.

<Measurement Chamber 42>

The measurement chamber 42 stores the gas detection element by fixing the support of the element. Gas is supplied to the inside of the chamber from the gas generation unit along the arrow. The gas supplied from the gas generation unit 41 flows inside the chamber, is brought into contact with the gas detection element, and is subsequently discharged outside of the chamber.

<Gas Concentration Meter 43>

A gas concentration meter 43 is a device for monitoring the concentration of the gas flowing inside the chamber. The device was installed for the purpose of checking that the target gas is flowing. As the gas concentration meter 43, Tiger (PID-type VOC concentration meter) manufactured by Riken Keiki Co., Ltd. was used.

<First Signal Applying Means 44 and Resonant Frequency Measuring Means 44>

An impedance analyzer (4294A, manufactured by Agilent Technologies, Inc.) was used as the transmission source of the first signal (alternating current voltage) for resonance driving and as a resonance frequency measuring device of the dielectric sensor. The analyzer is connected to the electrodes of the gas detection element 46 stored in the chamber.

<Second Signal Applying Means 45>

As a transmission source of the second signal (alternating current voltage) for heating the dielectric sensor, a combination of a function generator (FG410, manufactured by Yokogawa Meters & Instruments Corporation) and an amplifier (4005, manufactured by NF Circuit Design Block Co., Ltd.) were used in combination.

In FIG. 3, wiring for applying the first signal to the electrodes of the gas detection element is illustrated, but in a case where the second signal is applied, the connection between the electrodes of the gas detection element 46 and the first signal applying means 44 illustrated in FIG. 3 was switched to the connection between the electrodes of the gas detection element 46 and the second signal applying means 45.

Test Example 1

The gas detection element was set in the measurement chamber, and the inside of the chamber was evacuated to remove moisture and the like. Only nitrogen gas was supplied from the gas generation unit, and the pressure in the chamber was atmospheric pressure. While flowing nitrogen gas into the chamber, the first signal (alternating current voltage, 200 to 400 kHz scan 0.1 Vrms sine wave) was applied from an impedance analyzer to measure the resonance frequency of the dielectric sensor to be resonantly driven. The measured frequency was the resonant frequency (reference frequency) in a state in which detection target gas was absent.

Subsequently, the gas supplied from the gas generation unit was substituted with a mixed gas (1-butanol concentration: 10 ppm) of nitrogen gas and 1-butanol gas (boiling point: 117° C.), and the resonant frequency of the dielectric sensor resonantly driven by application of the first signal was measured. The resonant frequency at which the measured value of the resonance frequency was stabilized was the resonance frequency in a case where 10 ppm of 1-butanol gas was present.

Subsequently, the gas supply was stopped, the upper lid of the chamber was removed, and simultaneously, a signal applied between the electrodes was switched from the first signal supplied from the impedance analyzer to the second signal (alternating current voltage, 1 MHz 16 Vrms square wave) supplied from the function generator). The dielectric sensor was heated to 120° C. by the second signal.

After the second signal was applied for a predetermined period of time, the second signal was switched to the first signal again, and the resonant frequency of the dielectric sensor was measured.

The above test was repeated to determine the application time (1-butanol gas desorption completion time) of the second signal required for the measured resonant frequency to return to the same frequency as the reference frequency.

Comparative Test Example 1-1

In Test Example 1, after the upper lid of the chamber was removed, nitrogen gas was blown into the chamber without switching the first signal to the second signal. The air blowing time (1-butanol gas desorption completion time) required for the measured resonance frequency to return to the same frequency as the reference frequency was determined.

Comparative Test Example 1-2

In Comparative Test Example 1-1, after the upper lid of the chamber was removed, the chamber was left as it was without blowing nitrogen gas into the chamber. In this case, even in a case where the upper lid of the chamber was removed, and the chamber was left for one hour or more, the resonance frequency did not return to the same frequency as the reference frequency.

Results of Test Example 1 and Comparative Test Examples 1-1 and 1-2 are presented in the table below.

TABLE 1

Detection target gas: 1-butanol gas

|  | Test Example 1 | Comparative Test Example 1-1 | Comparative Test Example 1-2 |
|---|---|---|---|
| 1-butanol gas desorption completion time | 10 seconds | 290 seconds | one hour or more |

As presented in Table 1, the 1-butanol gas adsorbed on the gas adsorption film was not able to be sufficiently desorbed only by opening the chamber (Comparative Test Example 1-2). In a case where the chamber was opened and nitrogen gas was blown into the chamber, it took 290 seconds until the 1-butanol gas adsorbed on the gas adsorption film was completely desorbed and returned to the reference signal (Comparative Test Example 1-1).

Meanwhile, in a case where the second signal was applied between the electrodes and the dielectric sensor was heated to 120° C., the 1-butanol gas adsorbed on the gas adsorption film only by applying the second signal for an extremely short period of time of 10 seconds was able to be completely desorbed (Test Example 1).

Test Example 2

The acetone gas desorption completion time was determined in the same manner as in Test Example 1, except that the detection target gas was substituted from the 1-butanol gas (concentration: 10 ppm) to acetone gas (concentration: 10 ppm, boiling point of 56.3° C.), and the alternating current voltage of the second signal was changed to 1 MHz 13 Vrms square wave. The dielectric sensor was heated to 80° C. by the second signal.

Comparative Test Example 2-1

In Comparative Test Example 1-1, the acetone gas desorption completion time was determined in the same manner as in Comparative Test Example 1-1, except that the detection target gas was substituted from the 1-butanol gas (concentration: 10 ppm) to acetone gas (concentration: 10 ppm).

Comparative Test Example 2-2

In Comparative Test Example 1-2, the acetone gas desorption completion time was determined in the same manner as in Comparative Test Example 1-2, except that the detection target gas was substituted from the 1-butanol gas (concentration: 10 ppm) to acetone gas (concentration: 10 ppm).

The results of the test examples and comparative test examples above are provided in the table below.

TABLE 2

Detection target gas: acetone gas

|  | Test Example 2 | Comparative Test Example 2-1 | Comparative Test Example 2-2 |
|---|---|---|---|
| Acetone gas desorption completion time | 5 seconds | 30 seconds | 130 seconds |

As presented in Table 2 above, in a case where the chamber was opened, it took 130 seconds until the acetone gas adsorbed on the gas adsorption film was completely desorbed and returned to the reference signal (Comparative Test Example 2-2). In a case where the chamber was opened and nitrogen gas was blown into the chamber, it took 30 seconds until the acetone gas adsorbed on the gas adsorption film was completely desorbed and returned to the reference signal (Comparative Test Example 2-1).

Meanwhile, in a case where the second signal was applied between the electrodes, and the dielectric sensor was heated to 80° C., the acetone gas adsorbed on the gas adsorption film was able to be completely removed only by applying the second signal for an extremely short period of time of 5 seconds (Test Example 2).

The present invention has been described with the embodiments thereof, any details of the description of the present invention are not limited unless described otherwise, and it is obvious that the present invention is widely construed without departing from the spirit and gist of the present invention disclosed in the accompanying claims.

The present application claims the priority of JP2017-063604 filed in Japan on Mar. 28, 2017, the contents of which are incorporated herein by reference, as a part of the description of the present specification.

EXPLANATION OF REFERENCES

1: support (substrate)
2: first electrode
3: dielectric sensor
4: second electrode
5: gas adsorption film
21: $SiO_2$ film
22: Si film
23: $SiO_2$ film
24: Si film
25: first electrode
26: PZTN film
27, 28, 31, 32, 33: resist
29: contact with lower electrode
30: second electrode 41: gas generation unit
42: measurement chamber
43: gas concentration meter
44: first signal applying means and resonant frequency measuring means
45: second signal applying means
46: gas detection element

What is claimed is:

1. A gas detection method using a gas detection element obtained by laminating a fixed support, a first electrode, a dielectric sensor, a second electrode, and a gas adsorption film, in this order, the method comprising:
   a step of applying a first signal resonantly driving the dielectric sensor between electrodes of the first electrode and the second electrode, and detecting gas adsorbed on the gas adsorption film based on a change of a resonant frequency of the dielectric sensor; and
   a step of heating the dielectric sensor by applying a second signal between the electrodes, to thereby heat the second electrode on the dielectric sensor and the gas adsorption film on the second electrode after the detection of gas to desorb the gas adsorbed on the gas adsorption film.

2. The gas detection method according to claim 1, wherein the first signal and the second signal are alternating voltage voltages.

3. The gas detection method according to claim 2, wherein a frequency of the second signal is higher than a frequency of the first signal.

4. The gas detection method according to claim 2, wherein a voltage of the second signal is higher than a voltage of the first signal.

5. The gas detection method according to claim 1, wherein the dielectric sensor is formed of a ceramic dielectric material.

6. The gas detection method according to claim 1, wherein the dielectric sensor is formed of a dielectric material selected from lead zirconate titanate, lead zirconate titanate doped with niobium, zinc oxide, and aluminum nitride.

7. The gas detection method according to claim 1, wherein the gas adsorption film is formed of an organic material.

8. A gas detection method according to claim 1, using two or more gas detection elements, each of the gas detection elements being obtained by laminating a fixed support, a first electrode, a dielectric sensor, a second electrode, and a gas adsorption film, in this order, the method comprising:
   a step of applying a first signal resonantly driving the dielectric sensor between electrodes of the first electrode and the second electrode of each of the gas detection elements, and detecting gas adsorbed on the gas adsorption film of each of the gas detection elements based on a change of a resonant frequency of the dielectric sensor; and
   a step of heating the dielectric sensor of each of the gas detection elements, after the detection of gas, by applying a second signal between the electrodes, to thereby heat the second electrode on the dielectric sensor and the gas adsorption film on the second electrode to desorb the gas adsorbed on the gas adsorption film;
   wherein a constituent material forming the gas adsorption film of each of the gas detection elements is different from the other detection elements.

9. A gas detection system comprising:
   a gas detection element obtained by laminating a fixed support, a first electrode, a dielectric sensor, a second electrode, and a gas adsorption film, in this order;
   first signal applying means for applying a first signal resonantly driving the dielectric sensor between electrodes of the first electrode and the second electrode;
   resonant frequency measuring means for measuring resonant frequency of the dielectric sensor resonantly driven by application of the first signal; and
   second signal applying means for applying a second signal of heating the dielectric sensor between the electrodes of the first electrode and the second electrode, to thereby heat the second electrode on the dielectric sensor and the gas adsorption film on the second electrode.

10. The gas detection system according to claim 9, wherein the first signal and the second signal are alternating voltages.

11. The gas detection system according to claim 10, wherein a frequency of the second signal is higher than a frequency of the first signal.

12. The gas detection method according to claim 10, wherein a voltage of the second signal is higher than a voltage of the first signal.

13. The gas detection system according to claim 9, wherein the dielectric sensor is formed of a ceramic dielectric material.

14. The gas detection system according to claim 9, wherein the dielectric sensor is formed of a dielectric material selected from lead zirconate titanate, lead zirconate titanate doped with niobium, zinc oxide, and aluminum nitride.

15. The gas detection system according to claim 9, wherein the gas adsorption film is formed of an organic material.

16. A gas detection system comprising,
   two or more gas detection elements, each of the gas detection elements being obtained by laminating a fixed support, a first electrode, a dielectric sensor, a second electrode, and a gas adsorption film, in this order;
   first signal applying means for applying a first signal resonantly driving the dielectric sensor between electrodes of the first electrode and the second electrode of each of the gas detection elements;
   resonant frequency measuring means for measuring resonant frequency of each of the dielectric sensors resonantly driven by application of the first signal; and
   second signal applying means for applying a second signal of heating the each of the dielectric sensors between the electrodes of the first electrode and the second electrode of each of the dielectric sensors, to thereby heat the second electrode on the dielectric sensor and the gas adsorption film on the second electrode of each of the dielectric sensors;
   wherein a constituent material forming the gas adsorption film of each of the gas detection elements is different from the other detection elements.

* * * * *